United States Patent [19]

Marcus et al.

[11] Patent Number: 5,581,351
[45] Date of Patent: Dec. 3, 1996

[54] OPTICAL MONITOR FOR MEASURING THERMAL EXPANSION OF A ROTATING ROLLER

[75] Inventors: Michael A. Marcus, Honeoye Falls; Kenneth R. Schafer, Avon; Diane E. Kestner, Hilton, all of N.Y.

[73] Assignee: Eastman Kodak Company, Rochester, N.Y.

[21] Appl. No.: 389,841

[22] Filed: Feb. 15, 1995

Related U.S. Application Data

[62] Division of Ser. No. 276,745, Jul. 18, 1994, abandoned, which is a division of Ser. No. 199,419, Feb. 22, 1994, Pat. No. 5,392,123.

[51] Int. Cl.⁶ ............................ G01B 11/00; G01N 25/16
[52] U.S. Cl. ........................... 356/372; 356/384; 374/55; 374/153
[58] Field of Search ........................ 356/372, 373, 356/375, 376, 380, 381, 382, 384, 385, 426, 445–448, 355–358, 386; 250/560, 561; 33/700, 657, 501.03, 501.09; 118/665, 677, 679, 688, 691; 374/55, 120, 153, 161

[56] References Cited

U.S. PATENT DOCUMENTS

| | | | |
|---|---|---|---|
| 3,174,392 | 3/1965 | Räntsch | 356/384 |
| 3,419,330 | 12/1968 | Schneider | 356/106 |
| 3,565,531 | 2/1971 | Kane et al. | 356/381 |
| 3,775,012 | 11/1973 | Ling et al. | 72/35 |
| 3,792,928 | 2/1974 | Poilleux | 356/4 |
| 3,930,730 | 1/1976 | Laurens et al. | 356/357 |
| 3,940,608 | 2/1976 | Kissinger et al. | 250/227 |
| 4,009,965 | 3/1977 | Pryor | 356/109 |
| 4,038,555 | 7/1977 | Freeman | 250/238 |
| 4,053,237 | 10/1977 | Casey | 356/209 |
| 4,131,365 | 12/1978 | Pryor | 356/356 |
| 4,148,587 | 4/1979 | Erdmann et al. | 356/356 |
| 4,178,692 | 12/1979 | Schultz | 33/657 |
| 4,294,305 | 10/1981 | Oda | 33/657 |
| 4,295,278 | 10/1981 | Gloor | 33/657 |
| 4,344,232 | 8/1982 | Kihlstrom | 33/657 |
| 4,357,104 | 11/1982 | Davinson | 356/4 |
| 4,358,960 | 11/1982 | Porter | 73/705 |
| 4,489,495 | 12/1984 | Scheinecker | 33/657 |
| 4,653,905 | 3/1987 | Farrar et al. | 356/4 |
| 4,737,035 | 4/1988 | Aoki et al. | 356/445 |
| 4,746,211 | 5/1988 | Ruth et al. | 356/28.5 |
| 4,766,323 | 8/1988 | Franklin et al. | 250/561 |
| 4,821,544 | 4/1989 | Tamler et al. | 72/21 |
| 4,837,615 | 6/1989 | Boshier | 356/375 |
| 4,915,499 | 4/1990 | Gidon et al. | 356/28.5 |
| 5,162,131 | 11/1992 | Rantanen et al. | 118/679 |

FOREIGN PATENT DOCUMENTS

| | | | |
|---|---|---|---|
| 0280591 | 7/1990 | German Dem. Rep. | 356/381 |
| 0155204 | 12/1980 | Japan | 356/382 |
| 0084302 | 5/1982 | Japan | 356/384 |
| 0313705 | 12/1989 | Japan | 356/381 |
| 0284011 | 11/1990 | Japan | 356/381 |
| 0309204 | 12/1990 | Japan | 356/375 |
| 1783300 | 12/1992 | U.S.S.R. | 356/381 |
| 2066473 | 7/1981 | United Kingdom | 33/657 |

OTHER PUBLICATIONS

Michael A. Marcus, "Processing Monitoring and Control with Fiber Optics," SPIE, vol. 1368 Chemical, Biochemical, and Enivornmental Fiber Sensors II (1990), Eastman Kodak Company, Analytical Technology Division, Bldg. 23, Kodak Park, Rochester, NY 14652–4201 pp. 191–202.

*Primary Examiner*—Hoa Q. Pham
*Attorney, Agent, or Firm*—Mark G. Bocchetti; Carl F. Ruoff

[57] ABSTRACT

A gap measurement device includes a first roller and a second roller. The first roller and the second roller define a gap which varies due to thermal expansion and contraction of the rollers. A first optical probe measures a first distance to the first roller and generates a first-distance signal indicative of the first distance. A second optical probe measures a second distance to the second roller and generates a second-distance signal indicative of the second distance. An electronics module generates a gap-width signal indicative of the gap based on the first-distance signal and the second-distance signal. The invention can also measure roller velocity, roller runout, roller registration, and the thickness of liquid on a roller.

9 Claims, 14 Drawing Sheets

OPTICAL MONITOR FOR MEASURING THERMAL EXPANSION OF A ROTATING ROLLER

This is a Divisional of application Ser. No. 08/276,745, filed Jul. 18, 1994, now abandoned, which is a Divisional of application Ser. No. 199,419 filed 22 Feb. 1994 now U.S. Pat. No. 5,392,123.

TECHNICAL FIELD

The invention is directed to an optical device for monitoring machinery. More specifically, the invention is directed to an optical device for monitoring certain physical parameters, such as roller thermal expansion, roller runout, and roller speed, during machinery operation to verify that the machinery is operating properly. The invention can be used, for example, to monitor machinery for manufacturing photographic film.

BACKGROUND OF THE INVENTION

Many manufacturing operations require that precise dimensions be maintained between various parts of production machinery. For example, in roll coating operations required during the manufacture of photographic film, subbing, or overcoat layers are applied to a moving web as the web passes through a coating station. The subbing layer thickness is controlled by passing the coated web through a gap formed by a pair of rollers. The gap spacing, and thus the thickness of the subbing layer, varies due to thermal expansion and contraction of the rollers as the rollers change temperature.

A conventional method of measuring the gap between rollers is performed using shims. These measurements take place while the rollers are stationary, with the machinery at a temperature other than its normal operating temperature, and with the access doors to the machinery open. Unfortunately, this conventional technique does not provide real-time measurement of the roller gap while the machinery is actually operating. Production quality could be improved if the gap between the rollers could be monitored in real time, while the machinery is at normal operating temperatures, and while the product is actually being manufactured.

Furthermore, in many manufacturing processes, such as photographic film subbing, flammable solvents are present. The presence of electrical signals in such an environment creates the possibility of fire or an explosion.

SUMMARY OF THE INVENTION

It is an object of the invention, therefore, to provide a machinery monitor which monitors machinery parameters in real time.

It is another object of the invention to provide a machinery monitor which operates safely in an environment containing flammable materials.

It is another object of the invention to accurately measure machinery parameters while the machinery is at normal operating temperatures.

Another object of the invention is to accurately measure roller gap widths in real time while the dimensions being measured are undergoing significant thermal expansion due to large changes in temperatures.

Yet another object of the invention is to provide a device for measuring the thickness of liquid on a roller.

A further object of the invention is to provide a device for measuring the rotational speed, runout, thermal expansion, and registration of a roller.

A further object of the invention is to provide a device for measuring relative registration of a pair, or multiple, rollers.

According to a first aspect of the invention there is provided a film subbing station which includes a first roller and a second roller. The first roller and the second roller define a gap therebetween which determines a subbing layer thickness. The gap varies due to thermal expansion of the first roller and the second roller. A first optical probe measures a first distance to the first roller and generates a first-distance signal indicative of the first distance. A second, optical probe measures a second distance to the second roller and generates a second-distance signal indicative of the second distance. An electronics module, which is coupled to the first optical-probe and to the second optical probe, generates a gap-width signal in real time which is indicative of the gap based on the first-distance signal and the second-distance signal.

According to a second aspect of the invention there is provided a liquid thickness measurement device which includes a roller having a wet region covered with liquid and a dry region not covered with liquid. A first optical probe measures a first-distance to the wet region and generates a first-distance signal indicative of the first distance. A second optical probe measures a second distance to the dry region and generates a second-distance signal indicative of the second distance. An electronics module generates a liquid-thickness signal indicative of the liquid thickness based on the first-distance signal and the second-distance signal.

According to a third aspect of the invention there is provided a method of measuring the runout of a roller. The method includes reflecting light off of the roller as the roller rotates and generating a first signal indicative of the intensity of light reflected off of the roller. A roller-runout signal indicative of the runout of the roller is generated based on variations in the amplitude of the first signal with time.

The invention can also be used to measure dimensional changes of a film web due to thermal expansion and contraction.

Other objects, features, and advantages of the invention will be apparent from the following detailed description of preferred embodiments of the invention.

BRIEF DESCRIPTION OF THE DRAWINGS

The invention will be described below in further detail with reference to the accompanying drawings, wherein.

DETAILED DESCRIPTION OF PREFERRED EMBODIMENTS

The present invention provides a method and apparatus for measuring machinery parameters in real time while the machinery is at normal operating temperatures. In a preferred embodiment, the invention measures thermal expansion of rollers in a production environment.

Figure 1:
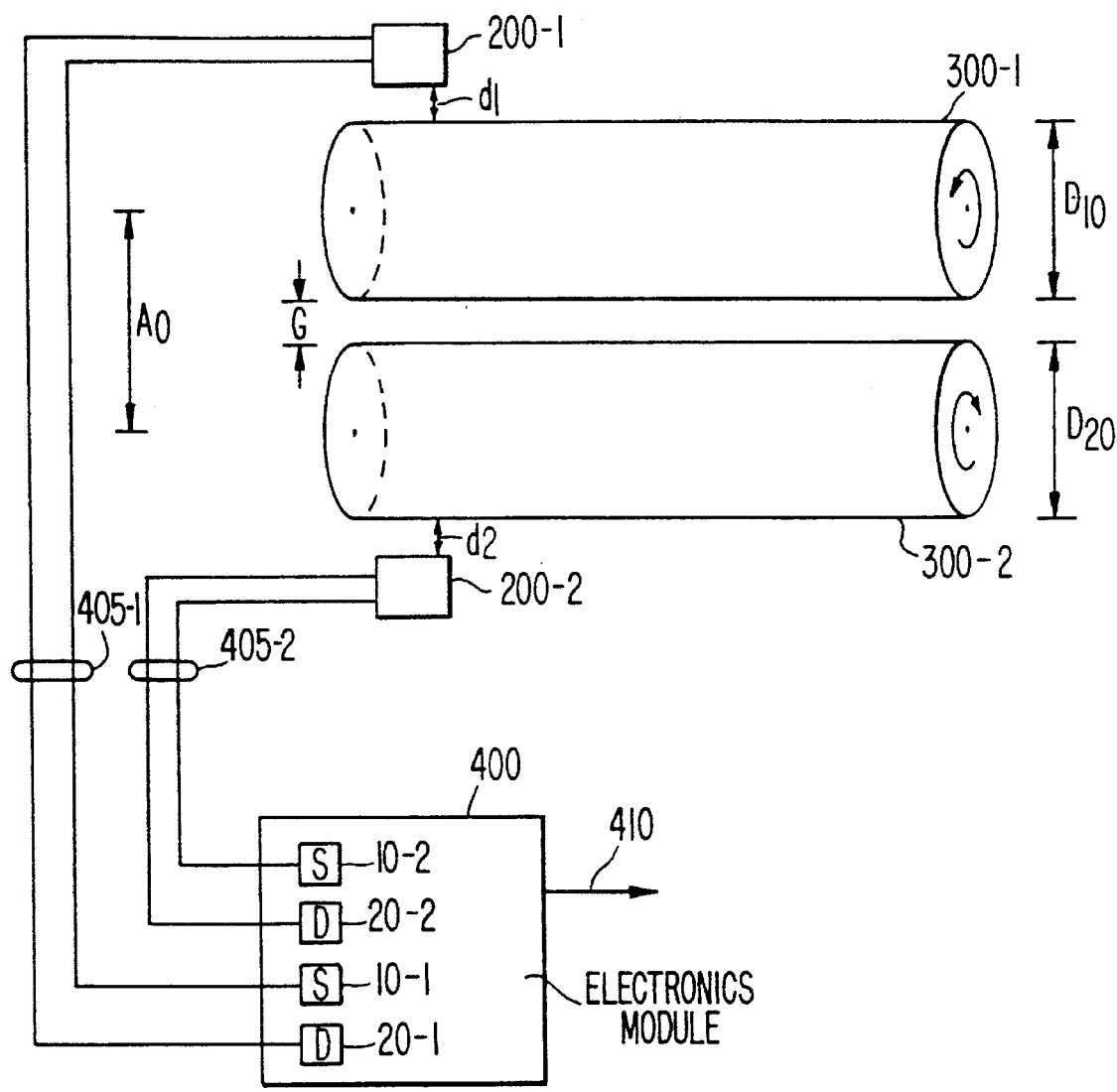
FIG. 1 illustrates a first preferred embodiment of the invention.
Figure 2:
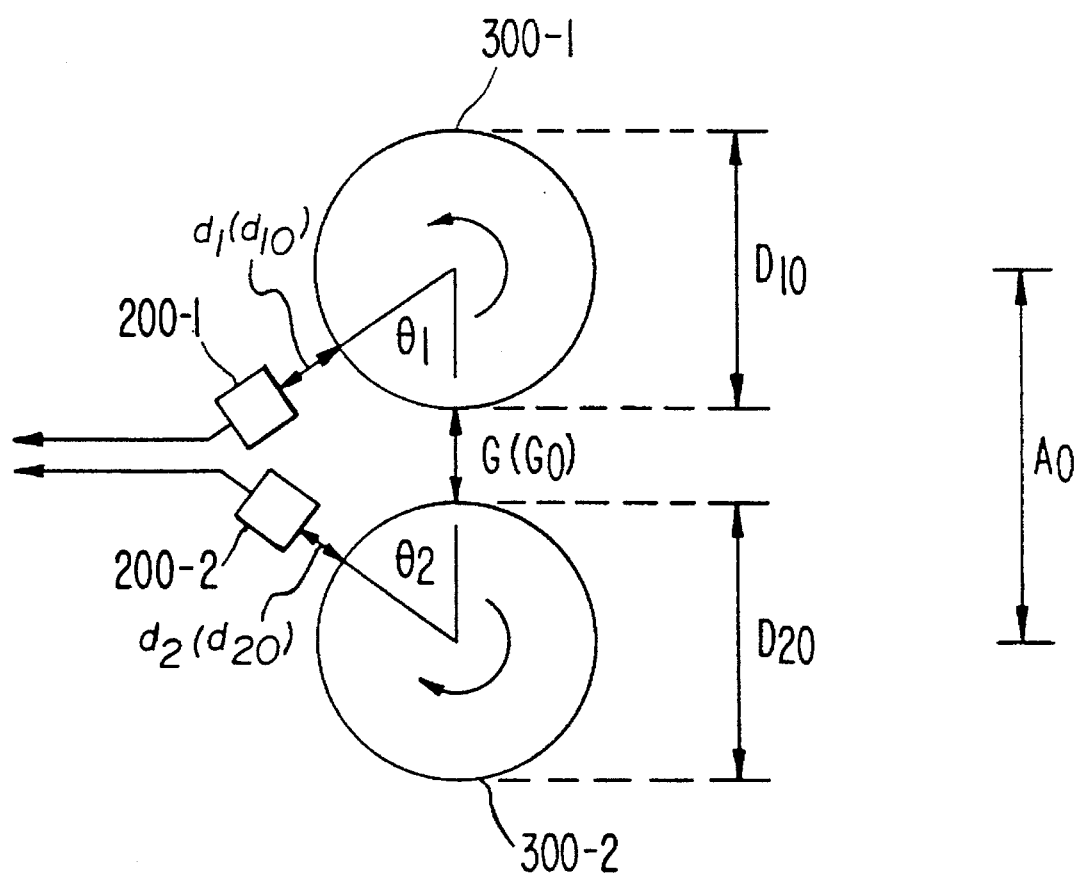
FIG. 2 illustrates a side view of the first preferred embodiment illustrated in FIG. 1.

FIG. 1 illustrates a first preferred embodiment of the invention. FIG. 2 illustrates a side view of the preferred embodiment illustrated in FIG. 1. In FIG. 1, optical probes 200-1 and 200-2 are shown out of position to improve the clarity of FIG. 1. The first preferred embodiment measures the gap G between two rollers 300-1 and 300-2 and outputs gap information on signal line 410. The outputted gap information is used by other equipment, which is not illustrated, to monitor and control production quality.

In the FIG. 1 embodiment, two fiber optic reflective probe transducers, or optical probes, 200-1 and 200-2 measure the distances $d_1$ and $d_2$ from the probe tips to rollers 300-1 and 300-2, respectively. Optical probe 200-1 measures distance $d_1$ and sends a signal indicative of $d_1$ to electronics module 400 via optical signal line 405-1. Optical probe 200-2 measures distance $d_2$ and sends a signal indicative of $d_2$ to electronics module 400 via optical signal line 405-2.

Electronics module 400 calculates the gap width G using the information received from optical signal lines 405-1 and 405-2 in accordance with the following technique. The invention determines the gap width G as a function of time by measuring $d_1$ and $d_2$ as a function of time. In FIG. 2, $A_0$ represents the roller center-to-center spacing at a reference temperature, $D_{10}$ and $D_{20}$ represent the diameters of the rollers at the reference temperature, $G_0$ represents the gap width at the reference temperature, $\theta_1$ and $\theta_2$ represent the angles the optical probes make with respect to a line joining the roller centers, and $d_{10}$ and $d_{20}$ represent the distances between the optical probe and the associated roller outer diameter at the reference temperature. The gap width G as a function of time is:

$$G(t) = G_0 + d_1(t) - d_{10} + d_2(t) - d_{20}$$

In the preferred embodiment, $d_1(t)$ and $d_2(t)$, and $d_{10}$ and $d_{20}$ are measured by averaging over multiple roller rotations for increased accuracy.

Optical probes 200-1 and 200-2 and optical signal lines 405-1 and 405-2 carry optical signals not electrical signals. Optical components are used in the vicinity of the rollers and associated machinery to eliminate the possibility of fires and explosions that would otherwise exist if electrical components were employed. The use of optical signal lines 405-1 and 405-2 permits electronics module 400 and other electrical components to be located away from flammable materials.

Figure 3:
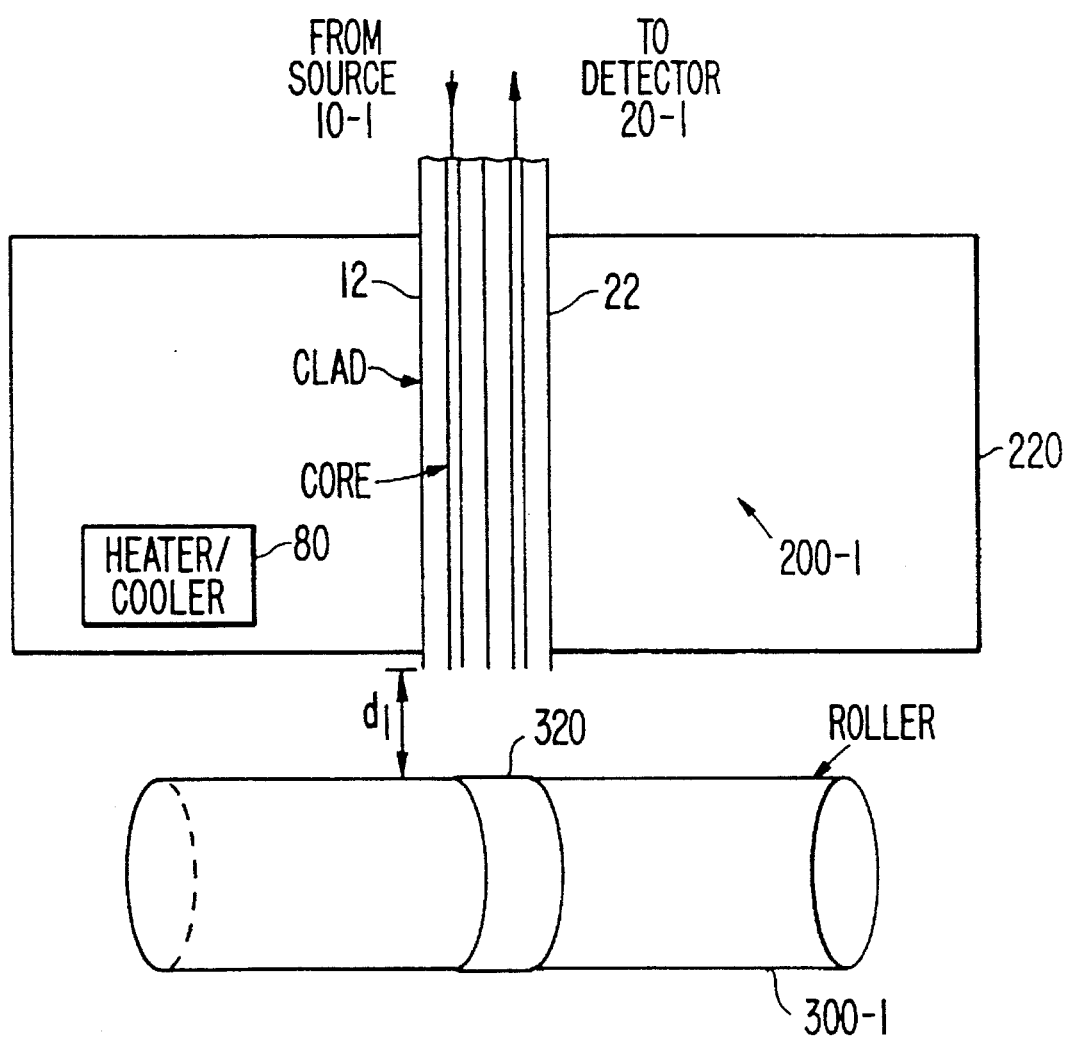
FIG. 3 illustrates a detailed design for optical probes of FIG. 1.

FIG. 3 illustrates a blown-up and more detailed view of optical probe 200-1. The design of optical probe 200-2 is similar to the design of optical probe 200-1 illustrated in FIG. 3. Optical probe 200-1 includes two optical fibers for transmitting and receiving light. A first optical fiber 12 is provided to transmit light onto roller 300-1. A second optical fiber 22 receives light which has been reflected off of roller 300-1. Optical fibers 12 and 22 are mounted parallel and adjacent to each other in a thin capillary tube. At the probe tip, the ends of the first and second optical fibers 12 and 22 are cleaved and polished flat. The end surface of optical fiber 12 is perpendicular to the longitudinal axis of fiber 12. The end surface of optical fiber 22 is perpendicular to the longitudinal axis of fiber 22.

Figure 4:
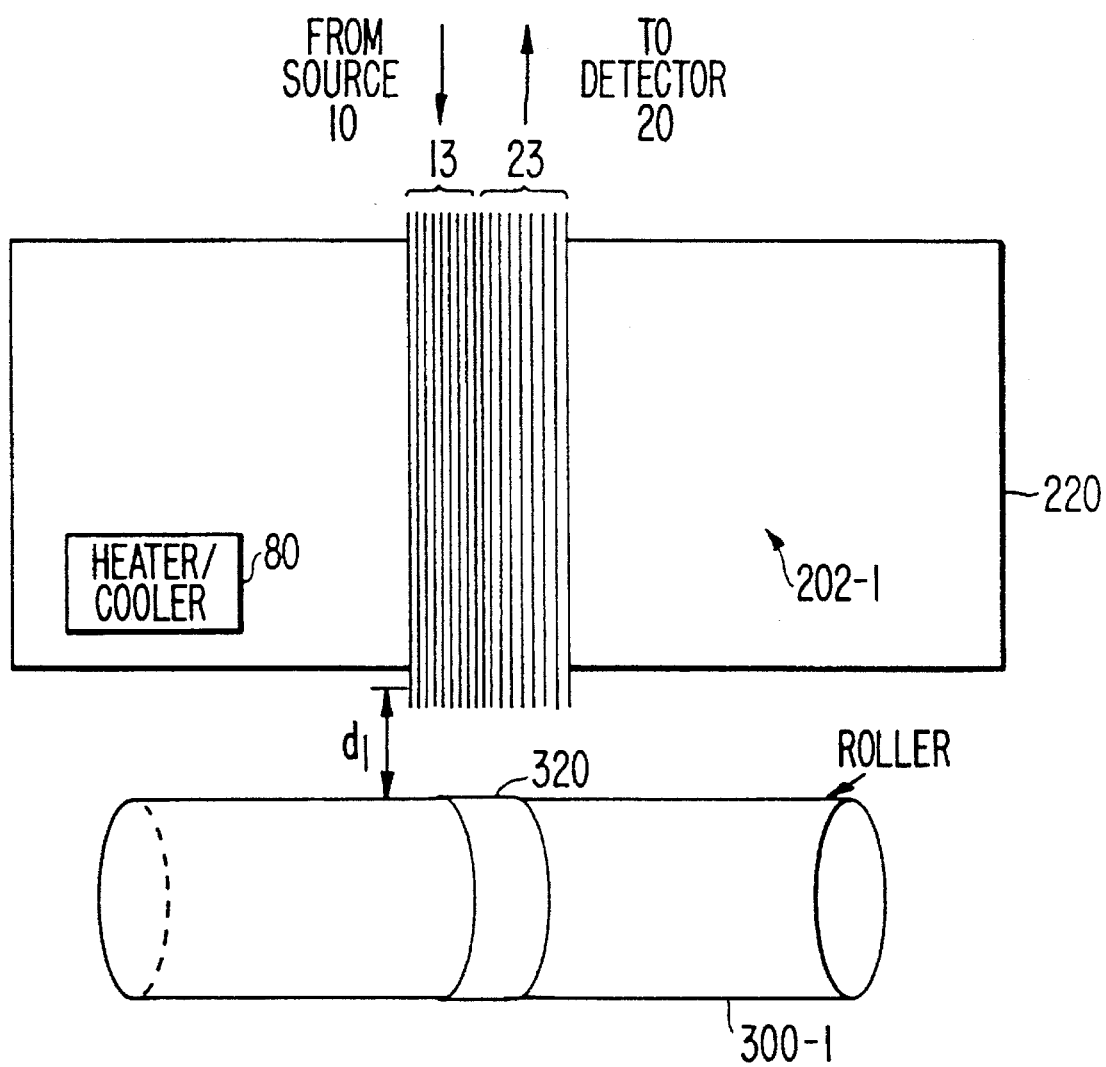
FIG. 4 illustrates a detailed alternative design for the optical probes of FIG. 1.

Additional information relating to optical sensors is set forth in an article entitled "Process monitoring and control with fiber optics" by Michael A. Marcus, which appeared in SPIE Vol. 1368, Chemical, Biochemical, and Environmental Fiber Sensors II (published in 1991). This SPIE document is incorporated herein by reference. Suitable dual fiber optical probes are manufactured by C-Technologies (model number MLA-2-2-102). It is understood that single fiber optical probes, dual fiber optical probes, or fiber bundles can be employed for optical probes 200-1 and 200-2. A bundle is a group of fibers which are surrounded by a single protective sheath and coupled together to the light source, the photodetector, or both the light source and the photodetector. FIG. 4 illustrates an optical probe 202-1 which employs bundles 13 and 23 to measure the distance $d_1$. The fibers can be single mode or multimode step index or graded index.

The light that is to be reflected off of roller 300-1 is generated by LED (light emitting diode) source 10-1, and passes through optical fiber 12 to the roller, or film, surface. In the first preferred embodiment, source 10-1 is an infrared LED. A suitable source is manufactured by General Fiberoptics (LED number 80-0821-SMA). Although the description and claims may generally refer to a "light" source and to transmitted, reflected and detected "light" it is understood that this term applies to the broad spectrum of electromagnetic radiation and not necessarily to only the visible spectrum. Light that has been reflected off of roller 300-1 is received by second optical fiber 22, passes through optical fiber 22, and is detected in photodetector 20-1. Photodetector 20-1 converts the received optical signal into a photocurrent proportional to the reflected light intensity. In the first preferred embodiment, photodetector 20-1 is a PIN photodiode. A suitable detector is manufactured by United Detector Technologies (PIN number HR040-SMA).

Because the temperature in the vicinity of probe 200-1 can vary considerably during machinery operation, in the preferred embodiment the components for probe 200-1 are enclosed in a constant temperature fixture 220 to minimize variations in the optical signal due to probe thermal distortion which would otherwise result from the effects of changes in temperature on the optical probe components. Inaccuracies would result, for example, if optical fiber dimensions changed due to ambient temperature changes. The probe 200-1 is also provided with a thermoelectric heater/cooler 80 to maintain the temperature within the constant temperature fixture 220 constant. Heater/cooler 80 can be, for example, a thermal electric heater which is in good thermal contact With the optical components within the constant temperature fixture 220. Other techniques can be used to ensure that the probes remain in an isothermal environment. For example, the entire subbing station can be maintained at a constant temperature.

The roller 300-1 is provided with a reflective surface 320 below the optical probe tip. In the preferred embodiment, the reflective surface 320 is provided around the entire circumference of the roller. The reflective surface 320 is not required if the surface of the roller provides a suitable reflective surface. Light from first optical fiber 12 is reflected off of reflective surface 320. Reflected light from reflective Surface 320 which falls within the numerical aperture NA of second optical fiber 22 is transmitted to photodetector 20-1 and is detected by photodetector 20-1. Numerical aperture is a well-known parameter in the field of fiber optics and is a measure of the light acceptance cone of an optical fiber. If a suitable reflective surface is not present, the only detected signal will be from stray light. The photodetector 20-1 generates an electrical signal proportional to the intensity of light received at photodetector 20-1.

Figure 5:
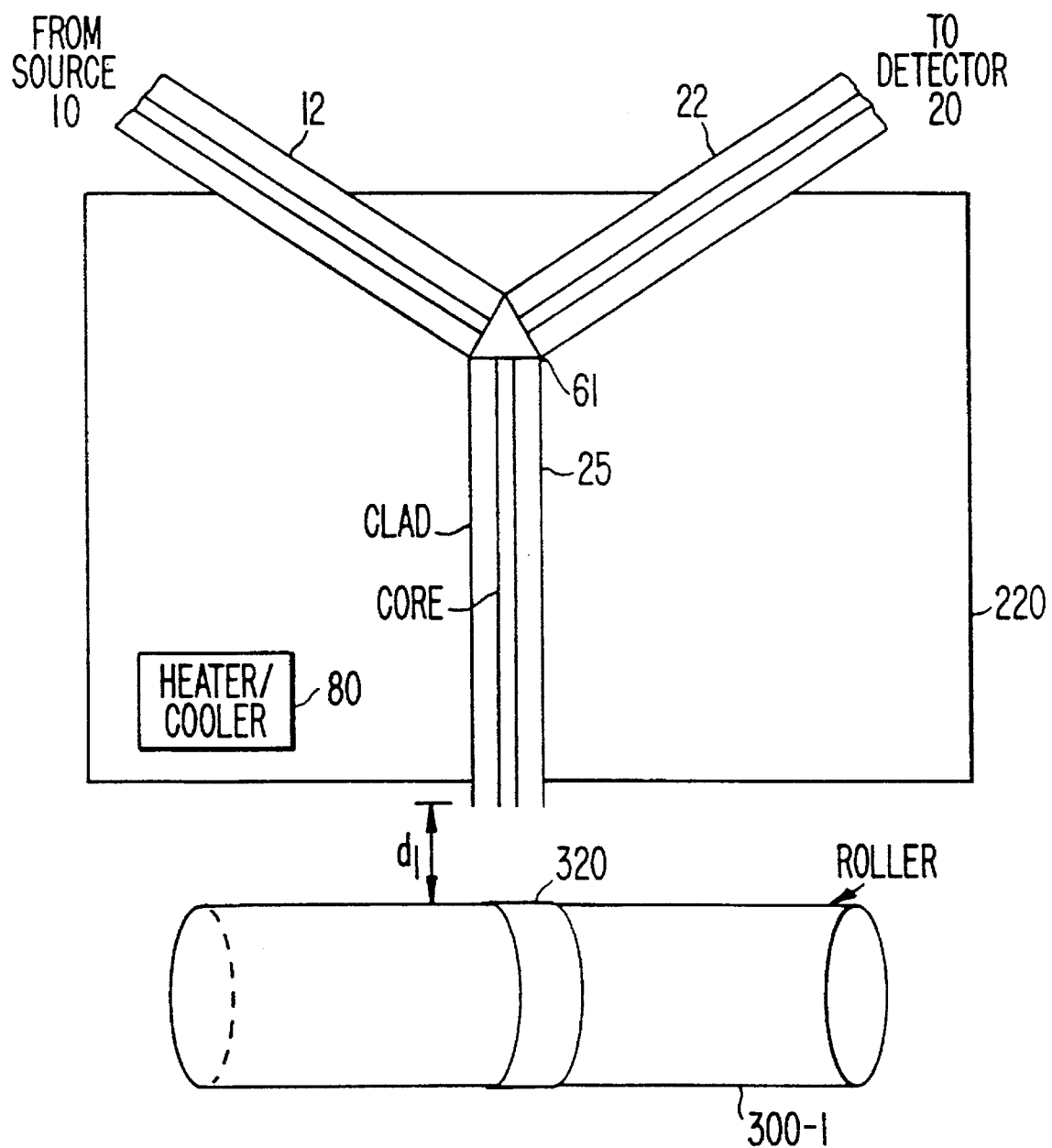
FIG. 5 illustrates another alternative design for the optical probes of FIG. 1.

The optical probe design of FIG. 3 can be modified by replacing the two optical fibers 12 and 22 with a single optical fiber, as illustrated in FIG. 5. In FIG. 5, a fiber 2:1 coupler 61 is placed in the input/output light path to enable a single optical fiber 25 to be used to transmit light to the roller and to receive light which has been reflected off of the roller.

Figure 6:
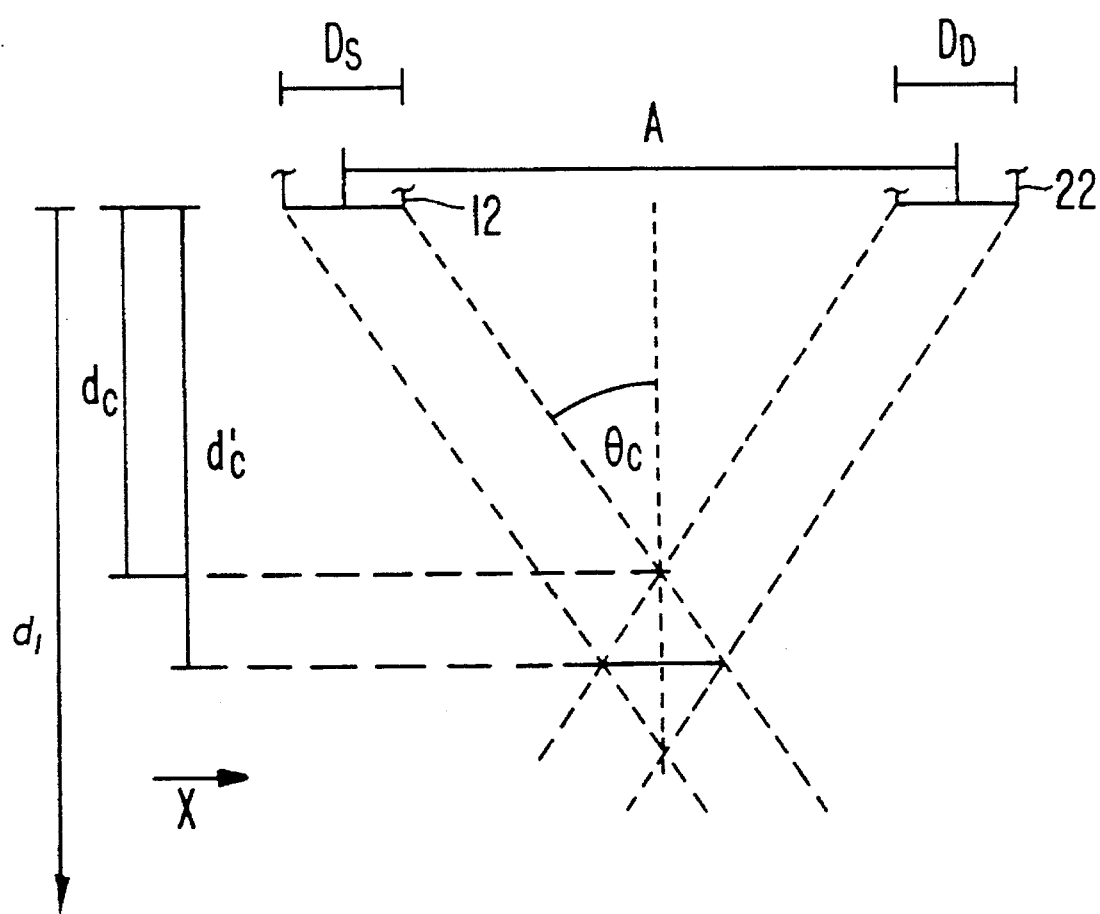
FIG. 6 illustrates optical path geometry for the optical probe and roller of FIG. 1.

FIG. 6 illustrates the optical path geometry for the optical probe and roller. The detected signal amplitude corresponding to the reflected light depends on the distance $d_1$ between the reflective surface 320 and the probe tip, the reflectivity of the reflective surface 320, the numerical aperture of optical fibers 12 and 22, the core diameters $D_S$ and $D_D$, the center-to-center fiber spacing A, and the angle the reflective surface 320 makes with respect to the optical probe surface. The dotted lines of FIG. 6 are drawn at a critical angle $\theta_c$ which represents the projection of the maximum acceptance cone in the plane of the figure.

Light that enters second optical fiber 22 results from a projection of core diameter $D_S$ from the core of the first optical fiber 12, to the reflective surface 320, and then back to the core of the second optical fiber 22. Three distinct distance regions occur in the FIG. 6 geometry. When $d_1 < d_c$ the electrical signal from photodetector 20-1 is zero. When $d_c \leq d_1 \leq d_c'$ the electrical signal increases rapidly as a function of distance. When $d_1 > d_c'$ the electrical signal falls off slowly with increasing distance.

Figure 7:
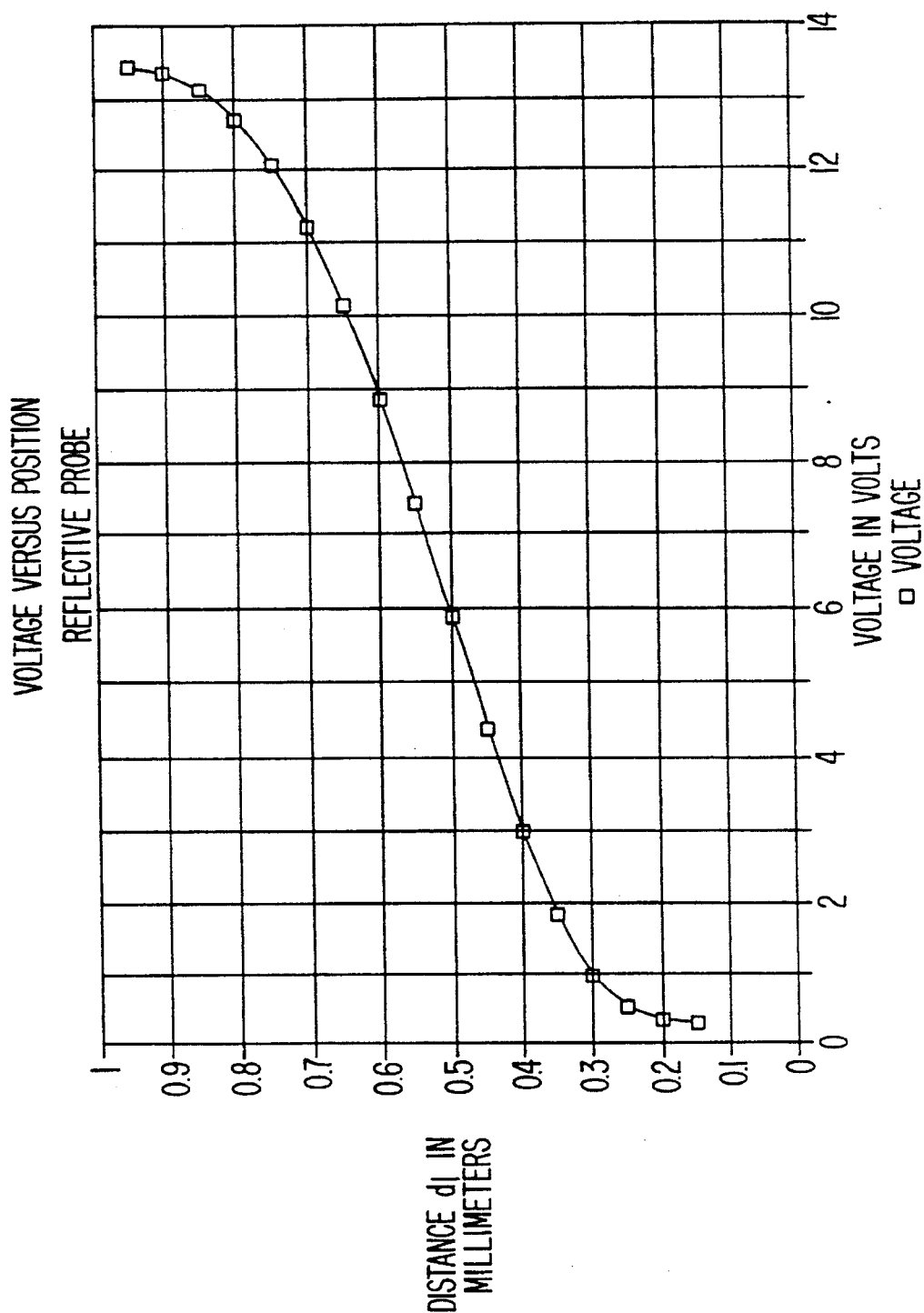
FIG. 7 illustrates a measured relationship between amplified photodetector voltage and the distance from the optical probe tip to the reflective surface.

FIG. 7 illustrates distance measurements in the first and second situations. FIG. 7 was generated using a 2 mW, 820 nm LED and two 200/240 μm fibers having a numerical aperture of 0.22 and a fiber center-to-center spacing of 350 μm. The horizontal axis in FIG. 7 represents the amplified voltage resulting from the light detection in photodetector 20-1. The vertical axis represents distance $d_1$. The signal for $d_1 \leq 0.15$ mm is zero. A maximum signal occurs at approximately d=1.0 mm. The measured amplified voltage characteristics illustrated in FIG. 7 agree with theoretical calculations.

As illustrated in FIG. 7, over the range of 0.45 mm $\leq d_1 \leq$ 0.65 mm the measured amplified signal is linear with respect to distance. This means that the amplified voltage can be used as an accurate measure for $d_1$. In this linear region, distance measurement has the greatest sensitivity.

If only a single optical fiber were used in the probe, as in FIG. 5, the maximum signal would occur at a distance to the reflective surface of zero, and the signal would fall off slowly with increasing distance.

The changes in gap G due to temperature changes in rollers 300-1 and 300-2 are relatively small. To make measurement of the thermal effects practical, machinery vibration, roller runout, roller reflectivity variation, roller rotation rate variation, and long term distance measurement stability should be considered. The term roller runout describes variation in the distance between the outer roller surface and the roller rotational axis as the roller rotates about its axis through a fixed angular position. Roller runout can vary as a function of the roller rotational angle as well as a shift in the central roller axis.

The effects of machinery vibration can be minimized by vibration isolation of the optical probe mounting. The effects of machinery vibration can also be compensated for by use of an additional probe which generates electrical signals indicative of mechanical vibration.

Figure 8:
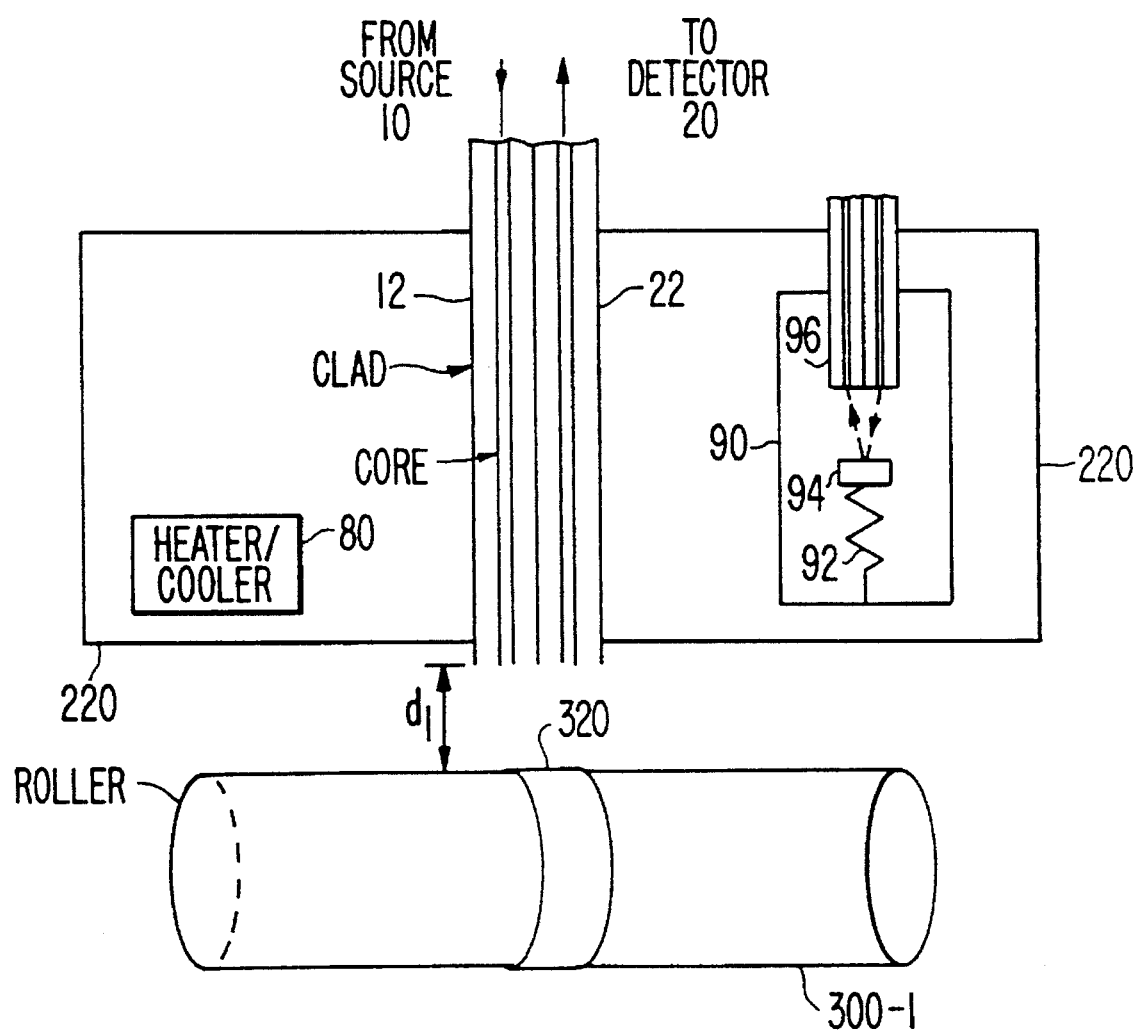
FIG. 8 illustrates a detailed design of an optical probe which includes an additional probe to compensate for mechanical vibration.

FIG. 8 illustrates an embodiment of the invention which includes an additional probe, vibration compensation probe 90, which generates optical signals indicative of the mechanical vibration of the optical probe 200-1. Vibration compensation probe 90 transmits these optical signals to electronics module 400. Electronics module 400 uses the signals from vibration compensation probe 90 to correct the signals from photodetector 20-1 for mechanical vibration. The vibration (displacement) signal is subtracted from the probe signal after the probe signal is corrected for reflectivity differences. Vibration compensation probe 90 is installed in the same housing that supports the components required to measure distance $d_1$.

Vibration compensation probe 90 includes a spring 92 having a spring constant k, a mass 94 having a reflective surface at an end of spring 92 and having a mass M, and probe 96. Probe 96 is positioned to reflect light off of the reflective surface of mass 94. Probe 96 is attached rigidly to the other components making up the optical probe at an offset distance $Z_0$ from the top flat reflective surface of mass 94. Spring 92 is constrained to move along only a single axis and has a fundamental resonance frequency above the expected vibration frequencies of the machinery.

When the spring 92 is positioned vertically, the acceleration a of the vibration compensation probe 90 is determined from the following equation:

$$a - g = -\frac{k(Z - Z_o)}{M}$$

where Z is the distance measured by probe 96 and g is the acceleration of gravity.

Figure 9:
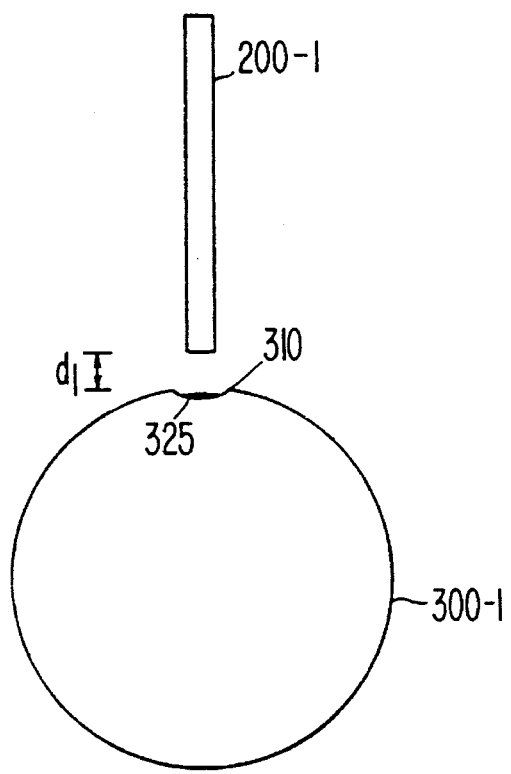
FIG. 9 illustrates a roller modification for measuring roller thermal expansion, roller speed, and roller runout.

Roller runout can be measured, and thus compensated for, even if the rollers are slipping, that is, even if roller speed is not constant. FIG. 9 illustrates a modification to roller 300-1 for measuring roller thermal expansion, roller speed, and roller runout. In a preferred embodiment, reflective material 325 is installed at a roller reference spot, or reference notch, 310 which is machined into the roller edge. The reflective material 325 is not required if the Surface of the roller provides a suitable reflective surface.

A reference mark is needed once per rotation. The reference mark can be provided by providing a notch or a bump in the roller or by placing a small strip of material with a different reflectivity over the roller. Depending upon the reflectively difference and on whether a notch or a bump is used as a reference mark, the reference mark will provide a local maximum or a local minimum in the signal intensity. The reference mark is designed to produce a variation larger than expected variations due to roller runout. The reference mark, notch, or strip can be extremely narrow, for example, one millimeter or less, as long as it is larger than the core diameter of the sensing fiber(s).

As the roller 300-1 rotates and reference spot 310 comes into the field of view of optical probe 200-1, the electrical signal indicative of $d_1$ will periodically reach a local maximum or minimum when the reference spot 310 is perpendicular to the fiber axis of optical probe 200-1. This local maximum or minimum is located electronically by electronics module 400 during every roller cycle to provide registration, that is, to provide an indication of the angular rotation of the roller. The amplitude of the signal at this local maximum or minimum corresponds to distance $d_1$ between optical probe 200-1 and reference spot 310 when reference spot 310 is perpendicular to the fiber axis of optical probe 200-1. The roller diameter over time is calculated by measuring local maxima or minima in the $d_1$ signal over time and by calculating the average of the $d_1$ signal for each roller rotation. Thermal expansion is determined in electronics module 400 by comparing the roller diameter at successive time intervals. These techniques minimize any potential inaccuracies which might otherwise result from reflectivity differences at different locations on the roller.

Measurement of the time interval, or periodicity, between reference spot measurements also provides an accurate measurement of roller speed. Bumps or any other abrupt change in the diameter of the roller can also be used to generate a periodic signal for speed measurement.

The difference between the maximum reflected signal intensity (when light is not being reflected off of reference spot 310) and the minimum reflected signal intensity (when light is not being reflected off of reference spot 310) provides an accurate measurement of roller runout. This difference can be measured for each roller rotation or over a number of roller rotations. Alternatively, the effect of runout on gap measurement can be eliminated by averaging the $d_1$ and $d_2$ signals whole number of roller rotations.

Properties of the light source may drift over time. To ensure long term stability and accurate measurement over time intensity measurements of the light source are performed.

Figure 10:
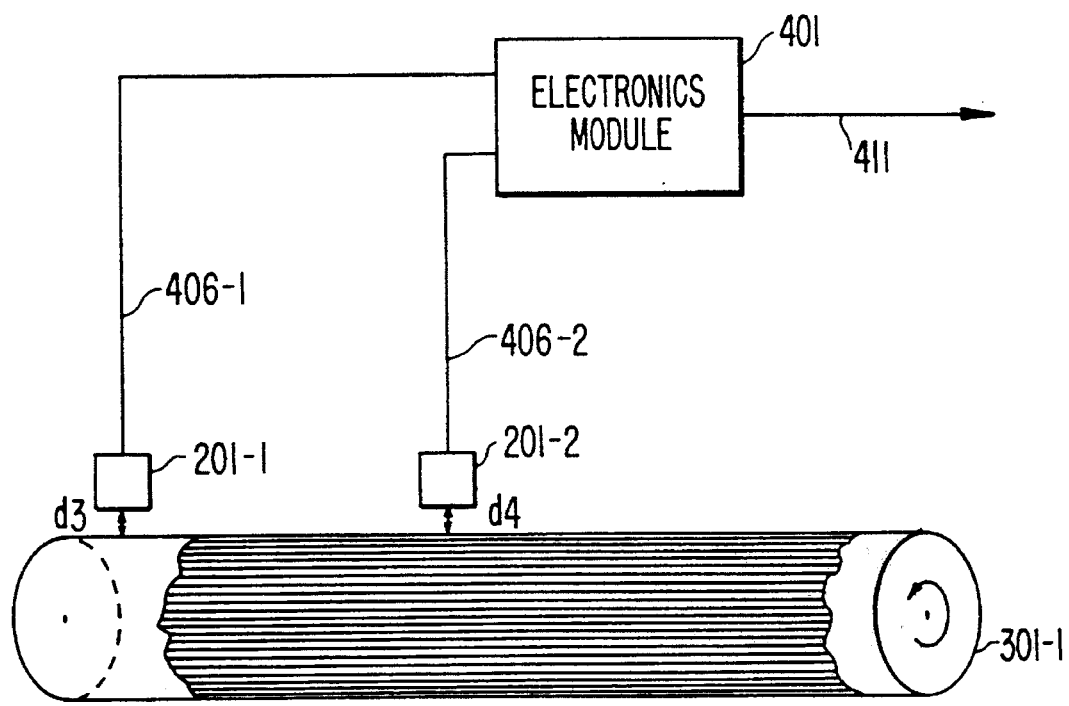
FIG. 10 illustrates a preferred embodiment of the invention for measuring liquid thickness variations.

The instant invention can also be used to determine the liquid thickness on a roller by comparing distance measurements for wet and dry regions. FIG. 10 illustrates a preferred embodiment for measuring liquid thickness. In the FIG. 10 embodiment, an optical probe 201-1 measures distance $d_3$ to a dry region of roller 301-1 and optical probe 201-2 measures distance $d_4$ to a wet region of roller 301-1. Electronics module 401 calculates the liquid thickness by subtracting $d_4$ from $d_3$. The reflectivity of the wet material must usually be known to accurately perform this measurement.

Figure 11:
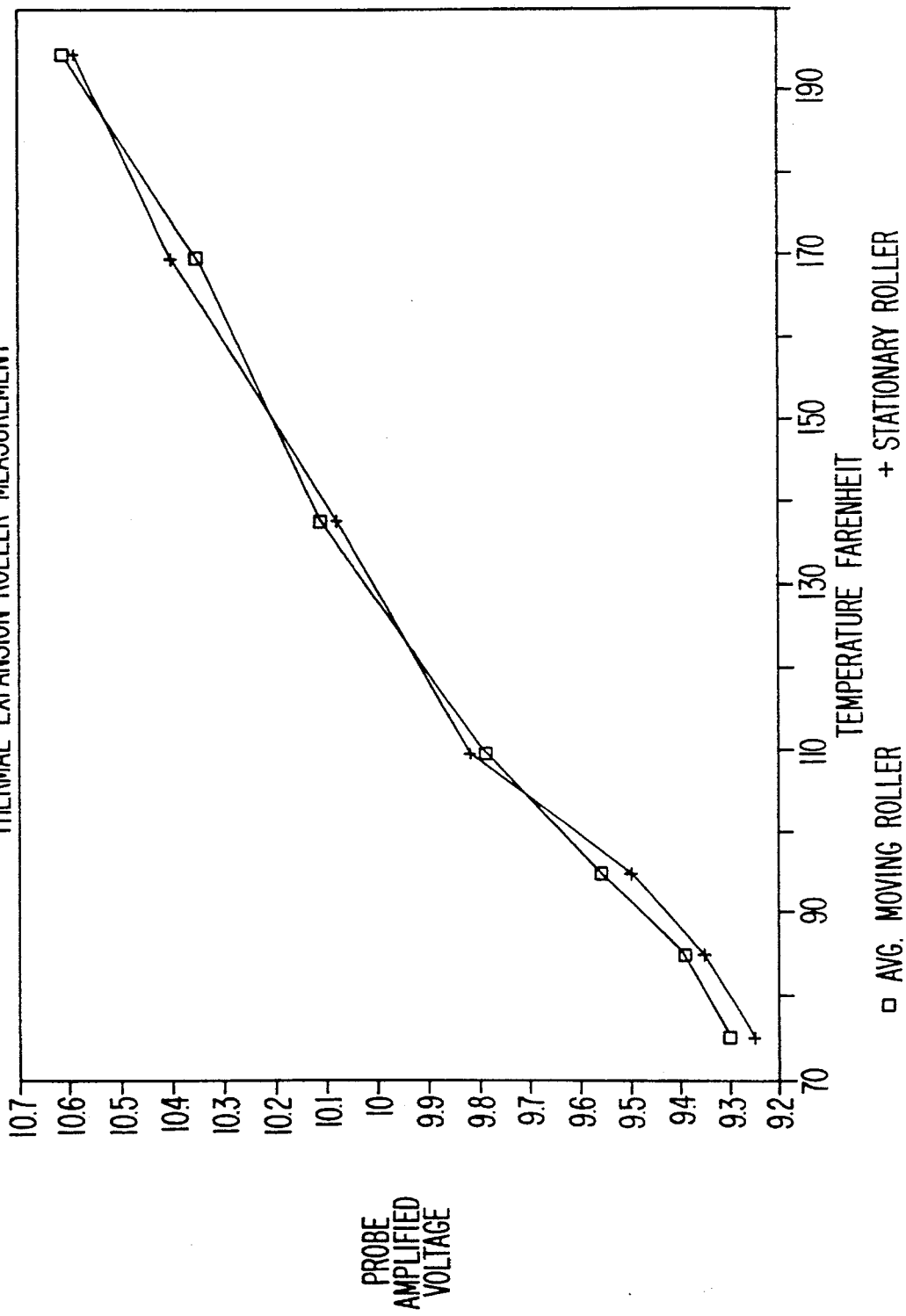
FIG. 11 illustrates how optical probe amplified voltage varied with roller temperature during experimental testing of the invention.

Real-time measurements were performed with a subbing station 8" diameter roller to confirm proper operation of the invention. During this testing the output of the photodetector was input to an oscilloscope and to a digital voltmeter for data processing. FIG. 11 illustrates how amplified voltage varied with roller temperature for both a stationary roller and for a moving roller. The data for the moving roller was obtained by averaging the signal over multiple roller cycles to average out the effects of roller runout.

In FIG. 11, a change in signal amplitude of 0.30 V corresponds to a one mil dimensional change. For a 120° F. temperature variation from 75° F. to 195° F. a voltage difference of 1.35 V was observed. This voltage difference is due to thermal expansion of the roller and corresponds to a thermal expansion of 4.5 mils between 75° F. and 195° F. The thermal expansion measured by the invention, 4.5 mils, is in excellent agreement with a predicted thermal expansion of 4.6 mils.

Figure 12:
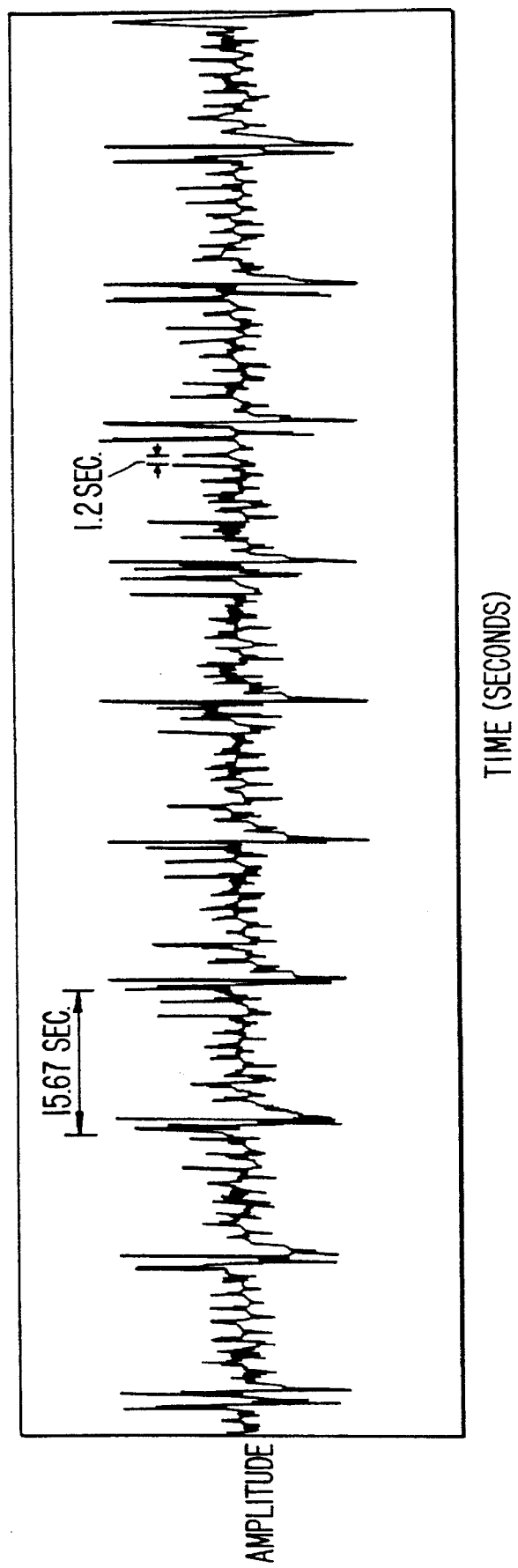
FIG. 12 illustrates an output signal from an optical probe.
Figure 13:
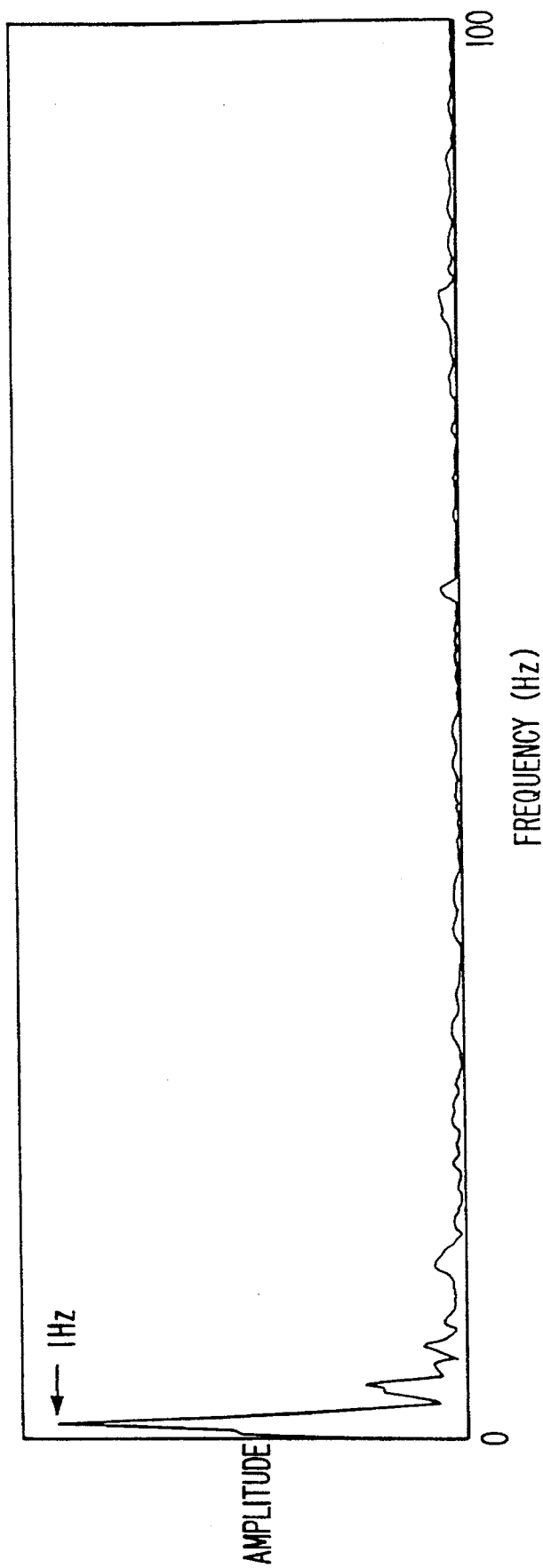
FIG. 13 illustrates a Fourier transform plot of the output of FIG. 12.

FIGS. 12 and 13 illustrate test data. FIG. 12 illustrates an output signal from an optical probe in an arrangement in which a piece of tape was used as a reference spot. In FIG. 12, the signal peaks occur at an interval of 15.67 seconds, indicating that a complete roller rotation occurs every 15.67 seconds. FIG. 13 illustrates a Fourier transform plot of the output of FIG. 12. The Fourier transform plot provides vibrational characteristics as a function of frequency. Roller runout data can be monitored over time to monitor roller operation.

Figure 14:
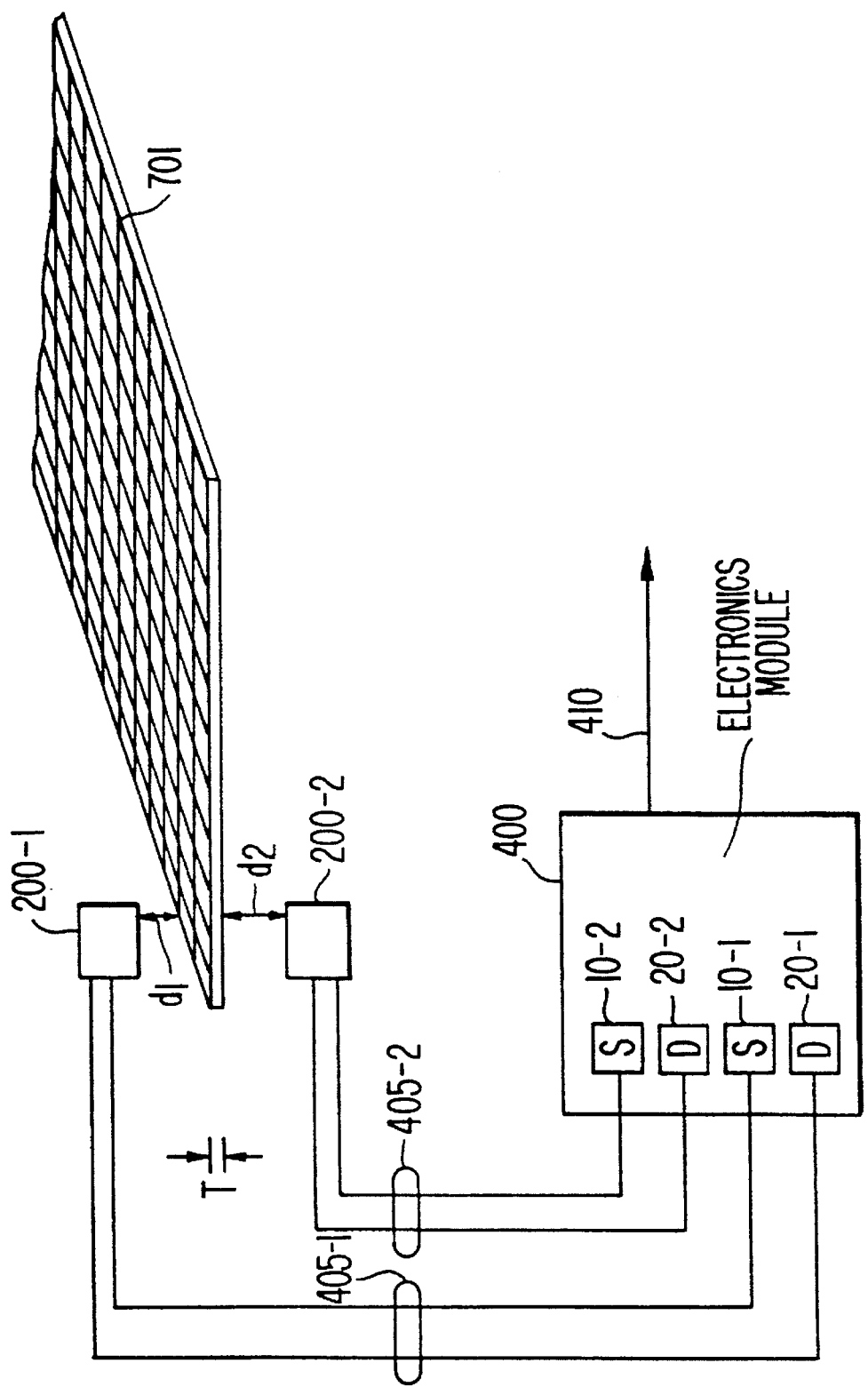
FIG. 14 illustrates a preferred embodiment for measuring thermal expansion of film web material.

The invention can also be used to measure thermal expansion of film web material in the thickness dimension. For example, FIG. 14 illustrates a preferred embodiment for measuring changes in the thickness T of film web 701 due to temperature changes by measuring changes in the sum of $d_1$ and $d_2$. Distance $d_1$ is measured to a first, or top, portion of film web 701 and distance $d_2$ is measured to a second, or bottom, portion of film web 701.

Figure 15:
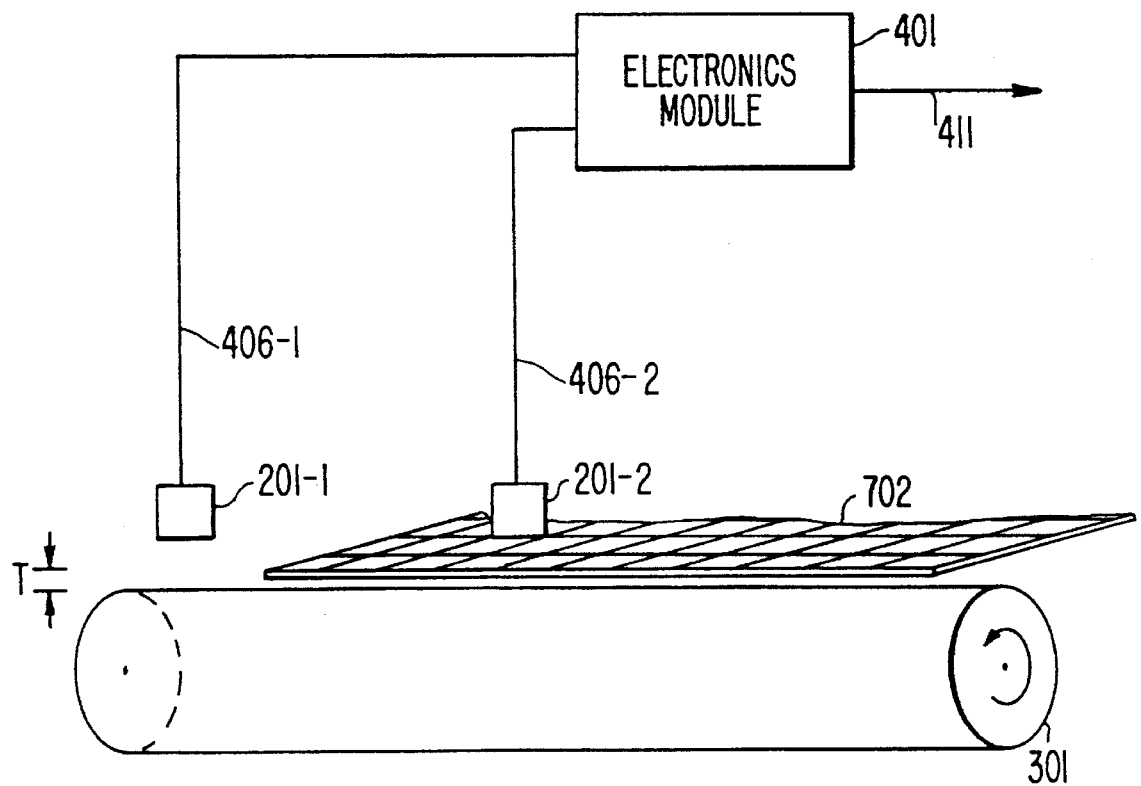
FIG. 15 illustrates another preferred embodiment for measuring thermal expansion of film web material.

FIG. 15 illustrates a preferred embodiment for measuring changes in the thickness T of film web 702 due to temperature changes. In FIG. 15, film web 702 is in contact with roller 301 and electronics module 401 calculates thickness T by subtracting the web distance signal measured by probe 201-2 from the roller distance signal measured by probe 201-1.

The invention has been described above with reference to certain specific implementations of the invention. However, the invention is not limited to the specific implementations described above. Modifications will be apparent to those skilled in the field in light of the above teachings. The Scope of the invention, therefore, is defined in the following claims.

What is claimed is:

1. A method of monitoring thermal expansion of a rotating roller, comprising the steps of:

(a) providing a roller whose reflectivity varies on at least one point around a circumference of said roller;

(b) rotating said roller;

(c) emitting light from an optical probe toward said circumference;

(d) measuring a cycle period based on light reflected off said at least one point;

(e) maintaining said optical probe in an isothermal environment;

(f) reflecting light from said optical probe off of said circumference as said roller rotates and generating a registration signal based on the intensity of light reflected off of said circumference at said at least one point; and (g) generating a thermal expansion/contraction signal indicative of thermal dimensional changes of said roller based on an average intensity per said cycle period of the light reflected off of said circumference.

2. A method as set forth in claim 1, wherein said average intensity is generated for each rotation of said roller.

3. A method of monitoring thermal expansion of a rotating roller as recited in claim 1, further comprising the steps of:

generating an optical vibration signal indicative of vibration of said optical probe;

compensating said thermal expansion/contraction signal for vibration of said optical probe with said optical vibration signal.

4. A method of monitoring thermal expansion of a rotating roller as recited in claim 1, further comprising the step of:

generating a roller speed signal indicative of the speed of said roller based on a periodicity of said registration signal.

5. A non-contact device for measuring dimensional changes due to at least one of thermal expansion and thermal contraction of a rotating roller, said device comprising:

an optical probe housed in an isothermal environment to measure a first distance to the rotating roller and to generate a first-distance signal indicative of said first distance, and to measure a second distance to the rotating roller at a later time to generate a second-distance signal indicative of said second distance; and an electronics module coupled to said optical probe to generate a thermal expansion/contraction signal indicative of at least one of said thermal expansion and thermal contraction based on said first-distance signal and said second-distance signal.

6. A non-contact device for measuring dimensional changes as recited in claim 5 wherein:

said electronics module generates a roller speed signal indicative of the speed of said roller based on a periodicity of said first-distance signal.

7. A non-contact device for measuring dimensional changes as recited in claim 5 wherein:

said first distance signal and said second distance signal are each averaged once per rotation of said roller.

8. A non-contact device for measuring dimensional changes as recited in claim 5 further comprising:

a vibration compensation probe coupled to said optical probe and to said electronics module, said vibration compensation probe generating an optical vibration signal indicative of vibration of said optical probe, thereby allowing said electronics module to compensate said first and second distance signals for the vibration.

9. A non-contact device for measuring dimensional changes as recited in claim 8 wherein said vibration compensation probe comprises:

a spring;

a reflective surface attached to said spring; and a probe to measure movement of said reflective surface, said probe transmitting said vibration signal in the form of an optical signal to said electronics module, said optical signal being indicative of said movement.

* * * * *